US007294709B2

(12) United States Patent
Dorsch et al.

(10) Patent No.: US 7,294,709 B2
(45) Date of Patent: Nov. 13, 2007

(54) **DETECTION OF *GIARDIA***

(75) Inventors: Matthias Rudolf Dorsch, New South Wales (AU); Duncan Adam Veal, New South Wales (AU)

(73) Assignee: Macquarie Research Ltd., New South Wales (AU)

( * ) Notice: Subject to any disclaimer, the term of this patent is extended or adjusted under 35 U.S.C. 154(b) by 199 days.

(21) Appl. No.: 10/795,442

(22) Filed: Mar. 9, 2004

(65) Prior Publication Data

US 2005/0032090 A1     Feb. 10, 2005

Related U.S. Application Data

(63) Continuation of application No. 10/018,211, filed as application No. PCT/AU00/00689 on Jun. 19, 2000, now abandoned.

(51) Int. Cl.
*C07H 21/04*    (2006.01)
*C12Q 1/68*    (2006.01)

(52) U.S. Cl. ............... 536/23.1; 536/24.3; 536/24.32; 536/25.32; 435/6; 435/91.1; 435/91.2

(58) Field of Classification Search .................. None
See application file for complete search history.

(56) References Cited

U.S. PATENT DOCUMENTS 5,558,989 A * 9/1996 Shah et al. ............... 425/6
5,888,736 A * 3/1999 Lacroix et al. ............ 435/6

FOREIGN PATENT DOCUMENTS

WO     WO 96/34978     11/1996

OTHER PUBLICATIONS

Sogin et al. (Genbank Accession No. M54878, Apr. 1993).*
Amann et al., Microbiological Reviews, Mar. 1995, pp. 143-169.
Deere et al., Journal of Applied Microbiology, 1998, 85, pp. 807-818.
Dorsch et al., Journal of Applied Microbiology 2001, 90, pp. 836-842.
Macechko et al., Microsc. Microanal. 1998, 4, pp. 397-403.
Rochelle et al., Applied and environmental Microbiology, 1997, 63, pp. 106-144.
Sogin et al., Science 1989, 243, pp. 75-77.
Van Keulen et al., J. Euk. Microbiol. 1995, 42(4), pp. 392-394.
Wallis et al., Applied and Environmental Microbiology, Aug. 1996, pp. 2789-2797.
Weiss et al., Molecular and Parasitology, 1992, 54, pp. 73-86.

* cited by examiner

*Primary Examiner*—Jeanine A. Goldberg
(74) *Attorney, Agent, or Firm*—Morgan, Lewis & Bockius LLP

(57) ABSTRACT

Oligonucleotide molecules for the detection of *Giardia lamblia* (*G. lamblia* which molecules hybridise under medium to high stringency conditions to unique 18S rDNA/ rRNA sequences of *G. lamblia*, and methods for the detection of the presence of viable cells of *G. lamblia* in samples using the oligonucleotide molecules.

5 Claims, No Drawings

SEQUENCE LISTING

```
<160> NUMBER OF SEQ ID NOS: 18

<210> SEQ ID NO 1
<211> LENGTH: 18
<212> TYPE: DNA
<213> ORGANISM: Giardia lamblia

<400> SEQUENCE: 1
gcgtcccggg tgagcggg                                                 18

<210> SEQ ID NO 2
<211> LENGTH: 18
<212> TYPE: DNA
<213> ORGANISM: Giardia lamblia

<400> SEQUENCE: 2
gcccgcgggc gcccgccc                                                 18

<210> SEQ ID NO 3
<211> LENGTH: 18
<212> TYPE: DNA
<213> ORGANISM: Giardia lamblia

<400> SEQUENCE: 3
tgggcccgcc tcgctcgc                                                 18

<210> SEQ ID NO 4
<211> LENGTH: 18
<212> TYPE: DNA
<213> ORGANISM: Giardia lamblia

<400> SEQUENCE: 4
cggcgggggg ccaactac                                                 18

<210> SEQ ID NO 5
<211> LENGTH: 18
<212> TYPE: DNA
<213> ORGANISM: Giardia lamblia
```

```
<400> SEQUENCE: 5
gcgggtccaa cgggcctg                                              18

<210> SEQ ID NO 6
<211> LENGTH: 18
<212> TYPE: DNA
<213> ORGANISM: Giardia lamblia

<400> SEQUENCE: 6
cggggctgcc gcggcgcg                                              18

<210> SEQ ID NO 7
<211> LENGTH: 18
<212> TYPE: DNA
<213> ORGANISM: Giardia lamblia

<400> SEQUENCE: 7
cccgctcacc cgggacgc                                              18

<210> SEQ ID NO 8
<211> LENGTH: 18
<212> TYPE: DNA
<213> ORGANISM: Giardia lamblia

<400> SEQUENCE: 8
gggcgggcgc ccgcgggc                                              18

<210> SEQ ID NO 9
<211> LENGTH: 18
<212> TYPE: DNA
<213> ORGANISM: Giardia lamblia

<400> SEQUENCE: 9
gcgagcgagg cgggccca                                              18

<210> SEQ ID NO 10
<211> LENGTH: 18
<212> TYPE: DNA
<213> ORGANISM: Giardia lamblia

<400> SEQUENCE: 10
gtagttggcc ccccgccg                                              18

<210> SEQ ID NO 11
<211> LENGTH: 18
<212> TYPE: DNA
<213> ORGANISM: Giardia lamblia

<400> SEQUENCE: 11
caggcccgtt ggacccgc                                              18

<210> SEQ ID NO 12
<211> LENGTH: 18
<212> TYPE: DNA
<213> ORGANISM: Giardia lamblia

<400> SEQUENCE: 12
cgcgccgcgg cagccccg                                              18

<210> SEQ ID NO 13
<211> LENGTH: 20
<212> TYPE: DNA
```

```
<213> ORGANISM: Giardia ardea

<400> SEQUENCE: 13
gcaggcgtcg cgcggcgctg                                          20

<210> SEQ ID NO 14
<211> LENGTH: 19
<212> TYPE: DNA
<213> ORGANISM: Giardia sp.

<400> SEQUENCE: 14
ggcgctgctg ctgcagtta                                           19

<210> SEQ ID NO 15
<211> LENGTH: 17
<212> TYPE: DNA
<213> ORGANISM: Giardia muris

<400> SEQUENCE: 15
ggagtcgaga cgtccag                                             17

<210> SEQ ID NO 16
<211> LENGTH: 18
<212> TYPE: DNA
<213> ORGANISM: Giardia microti

<400> SEQUENCE: 16
ctcgccgcgg cagccccg                                            18

<210> SEQ ID NO 17
<211> LENGTH: 23
<212> TYPE: DNA
<213> ORGANISM: Giardia ardea

<400> SEQUENCE: 17
tggacctacc gcccgggacg gcg                                      23

<210> SEQ ID NO 18
<211> LENGTH: 15
<212> TYPE: DNA
<213> ORGANISM: Giardia sp.

<400> SEQUENCE: 18
cgcccgggac gcgcg                                               15
```

DETECTION OF GIARDIA

This application is a Continuation of U.S. application Ser. No. 10/018,211, filed Dec. 18, 2001 now abandoned, which is a National Stage of PCT/AU00/00689 filed Jun. 19, 2000, which claims the benefit of Australian Application No. PQ1056. All of which are incorporated by reference in their entirety.

TECHNICAL FIELD

The present invention is directed to the detection of parasite pathogens, particularly *Giardia lamblia*, using molecular probes.

BACKGROUND ART

Fluorescent in situ hybridisation (FISH) employing nucleic acid probes is one of the most advanced techniques for detection and enumeration of microorganisms. The technique emerged in the early nineties and since then has been improved rapidly and is being used for a wide range of applications which include diagnostics in clinical microbiology and analysis of microbial community structure in environmental and industrial microbiology/biotechnology. Although widely used for bacteria, very few publications describe methods for detection and enumeration of protozoan pathogens. The design of oligonucleotide probes requires skill and experience to determine accessible regions of rRNA in native ribosomes. An additional problem of successful FISH for protozoa is the development of hybridisation protocols that allow oligonucleotide probes to penetrate protozoa cell walls which are fundamentally different to bacterial cell walls. Moreover, the composition of bacterial cell walls has been well documented whereas little knowledge exists about the structure of the cyst walls of protozoa like *Cryptosporidium* spp, *Giardia* spp and related organisms.

To date, monoclonal antibodies (mabs) are the most important and widely applied tool for detection of *Giardia* cysts in water samples. The vast majority of commercially available antibodies show a lack of specificity as the antibodies detect all *Giardia* spp including species that do not infect humans. As a positive antibody reaction does not allow any conclusion regarding the viability (infectivity) of the cysts, viability stains (DAPI, PI) have to be used in conjunction with antibodies.

Oligonucleotide probes for FISH have several advantages over mabs in that probes are significantly cheaper to produce and are more stable as probes can be. stored for long periods without loosing reactivity or specificity. Furthermore, correctly designed probes should only detect cysts of *Giardia lamblia* and no other species unable to infect humans. Probes target rRNA and will potentially only detect viable cysts which are able to cause infection. As non-viable (dead) cyst contain no or only small amounts of rRNA, it is envisaged that these cysts will not undergo detection.

The present inventors have developed specific oligonucleotides suitable for detection of potentially viable *Giardia* spp cysts and hybridisation protocols that allow permeabilization of the cyst walls and enable oligonucleotide probes to reach their ribosomal nucleic acid targets.

DISCLOSURE OF INVENTION

In a first aspect, the present invention consists in an oligonucleotide molecule for the detection of *Giardia lamblia* (*G. lamblia*), the oligonucleotide molecule hybridises to unique 18S rDNA/rRNA sequences of *G. lamblia*.

Preferably, the oligonucleotide molecule hybridises specifically to unique 18S rDNA/rRNA sequences of *G. lamblia* under medium to high stringency conditions (Sambrook et al., 1989 Molecular Cloning: A Laboratory Manual, Cold Spring Harbour Laboratory Press). In many cases, however, conditions of high stringency can be used to ensure specific hybridisation to unique *G. lamblia* 18S rDNA/rRNA sequences.

In a preferred embodiment of the first aspect of the present invention, the oligonucleotide molecule is selected from the group of oligonucleotides having one or more of the following nucleotide sequences:

| Giar-1 | GCG TCC CGG GTG AGC GGG | (SEQ ID NO: 1) |
| Giar-2 | GCC CGC GGG CGC CCG CCC | (SEQ ID NO: 2) |
| Giar-3 | TGG GCC CGC CTC GCT CGC | (SEQ ID NO: 3) |
| Giar-4 | CGG CGG GGG GCC AAC TAC | (SEQ ID NO: 4) |
| Giar-5 | GCG GGT CCA ACG GGC CTG | (SEQ ID NO: 5) |
| Giar-6 | CGG GGC TGC CGC GGC GCG | (SEQ ID NO: 6) | or comprising a part of the sequences, typically at least 10 bases in length, Giar-1 to Giar-6 above so as to allow specific hybridisation to unique 18S rRNA sequences of *G. lamblia*.

In a further preferred embodiment, the oligonucleotide molecules are Giar-4 or Giar-6.

Preferably, the oligonucleotide molecules according to the invention are detectably labelled so that the oligonucleotides may be utilised as probes in hybridisation assays. It will be appreciated, however, that oligonucleotide molecules which are not labelled may be used, for example, in a polymerase chain reaction (PCR) to amplify a part of the rDNA of *G. lamblia*.

Stringent conditions are usually defined as those that (1) employ low ionic strength and high temperature for washing, for example, 0.015 M NaCl/0.0015 M sodium citrate/0/1% NaDodSO$_4$ at 65° C.; (2) employ during hybridisation a denaturing agent such as formamide, for example, up to 50% (vol/vol) formamide with 0.1% bovine serum albumin, 0.1% Ficoll, 0.1% polyvinylpyrrolidone, 50 nM sodium phosphate buffer at pH 6.5 with 750 mM NaCl, 75 mM sodium citrate at 42° C.; or (3) employ up to 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Clarification of the term "18S rDNA/rRNA" for *Giardia lamblia* and *Giardia* spp. is provided as follows. The RNA molecule in question is very unusual. With approximately 1450 nucleotides, the 18S RNA molecule is significantly shorter than the 18S rRNA of other eukaryotes and in respect of sizes resembles the 16S rRNA of bacteria (Sogin et al. 1989 Phylogenetic meaning of the kingdom concept: An unusual ribosomal RNA from *Giardia lamblia*. Science 243: 75-77). However, as determined by sequence homology *Giardia* appears to be an eukaryote representing a phylogenetically 'ancient' group of species. In the following, the term "18S rRNA/DNA" will be used for all eukaryotic sequences that were examined for the purpose of designing *Giardia lamblia* specific probes.

In a second aspect, the present invention provides a method for the detection of the presence of viable cells of *G. lamblia* in a sample, the method comprising the steps of:
(a) adding to the sample a probe comprising a detectably labelled oligonucleotide molecule according to the first aspect of the present invention;
(b) allowing hybridisation of the probe to the 18S rDNA/rRNA of any *G. lamblia* cells present in the sample; and
(c) detecting hybridisation of the probe.

Detection of any hybridisation of the probe to 18S rDNA/rRNA in the sample is indicative of the presence of viable cells of *G. lamblia* in the sample.

The sample can be any sample where there is concern that *G. lamblia* may be present. Samples include environmental, water sources, waste materials, medical and body fluids. Examination of drinking water samples are particularly applicable for the present invention.

In a preferred embodiment, the method is used in combination with fluorescence in situ hybridisation (FISH) in which the oligonucleotide probe is labelled with a fluorochrome and after hybridisation, the resulting fluorescent cell is detected by epifluorescence microscopy or flow cytometry.

Suitable fluorochromes for the probes include but not limited to fluorescein isothiocyanate (FITC, green), cyanine dyes Cy2, Cy3, Cy3.5, Cy5, Cy5.5 (ranging from green to far red) or Texas Red. Other labels include radio-isotopes phosphorus $^{32}$P and $^{33}$P and sulfur $^{35}$S. Another option is conjugation of probes to biotin and then add streptavidin-linked horseradish peroxidase (HRP) to the hybridisation reaction in order to enhance the signal via tyramide signal amplification (TSA).

In order to improve the hybridisation of the probe to the nucleic acid of the cell, the present inventors have found that adding formamide (preferably around 20% v/v) to the hybridisation buffer increases the stringency sufficiently to eliminate cross reactions of the probes with *Giardia muris*). Other agents which act in a similar manner would also be suitable to assist in specific hybridisation.

In a further preferred embodiment of the second aspect of the present invention, several different oligonucleotide probes are used and are distinguished by the use of different labels on each probe. More preferably the oligonucleotide probes are labelled with different fluorochromes and detected by flow cytometry.

While it is preferred that the probes are fluorescently labelled, it is to be understood that other known forms of labelling may be used within the broad scope of the present invention. Examples of other forms of labelling are radioactivity and chemiluminescence.

In a third aspect, the present invention provides an oligonucleotide molecule which hybridizes to *G. lamblia* 18S rDNA/rRNA sequences under medium to high stringency conditions wherein the oligonucleotide molecules hybridizes to at least one of target regions of *G. lamblia* rDNA having the following nucleotide sequences:

| | |
|---|---|
| CCC GCT CAC CCG GGA CGC | (SEQ ID NO: 7) |
| GGG CGG GCG CCC GCG GGC | (SEQ ID NO: 8) |
| GCG AGC GAG GCG GGC CCA | (SEQ ID NO: 9) |
| GTA GTT GGC CCC CCG CCG | (SEQ ID NO: 10) |
| CAG GCC CGT TGG ACC CGC | (SEQ ID NO: 11) |
| CGC GCC GCG GCA GCC CCG | (SEQ ID NO: 12). |

The oligonucleotide molecules and methods of the present invention may be used to detect the presence in a sample of any type of viable cell of *G. lamblia*. Normally only oocysts will be found in environmental samples. Other cell types, trophozoites may, however, be found and detected in clinical samples.

The oligonucleotide probes according to the present invention have tested successfully in the inventors' laboratories. Probes were used on samples that underwent IMS, staining with fluorescently labelled antibodies and sorting of positive particles on a membrane via flow cytometry. FISH was then carried out with these membranes in order to determine species identity and viability of the cysts and the membranes examined by epi-fluorescence microscopy once the hybridisation reaction is completed.

Further, it has been established that the probes specifically detect cysts of *Giardia lamblia*. Weak cross reactions were observed when the probes were hybridised against cysts of the closely related species *Giardia muris*. Cross reactions were subsequently eliminated by modifying the hybridisation buffer in a manner that increases the stringency of the hybridisation.

The present inventors demonstrated earlier that an excellent correlation exists between the FISH signal intensity obtained from *Cryptosporidium parvum* oocysts and viability of the oocysts as measured by excystation (Vesey et al. 1995 The use of a ribosomal RNA targeted oligonucleotide probe for fluorescent labelling of viable *Cryptosporidium parvum* oocysts. *J. Appl. Microbiol.* 85: 429-440). It is likely that *Giardia* cysts having lost their viability through ageing, which includes degradation of the rRNAs, the target of the oligonucleotide probes, will not show any fluorescent signal.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any description of prior art documents herein is not an admission that the documents form part of the common general knowledge of the relevant art in Australia.

In order that the present invention may be more clearly understood, preferred forms will be described with reference to the following examples.

MODES FOR CARRYING OUT THE INVENTION

Design of Oligonucleotide Probes

A brief explanation of the systematics of the genus *Giardia* is provided as follows. *Giardia lamblia* is the only species of the genus that is known to cause disease in humans. Some controversy still surrounds the systematics of the species which is also referred to as *Giardia duodenalis* or *Giardia intestinalis* (Lu et al. 1998 Molecular comparison of *Giardia lamblia* isolates. Int. J. Parasitol. 28: 1341-1345). Other representatives of the genus *Giardia* described to date are *Giardia agilis* from amphibians and *Giardia muris* from rodents, birds and reptiles (Meyer 1994 *Giardia* as an organism. P 3-13. In: RCA. Thompson, J. A. Reynoldsen, A. J. Lymbery (eds.) *Giardia:* From molecules to disease. CAB International, Wallingford, Oxon, UK), *Giardia ardea* from herons (Erlandsen et al. 1990 Axenic culture and characterization of *Giardia ardea* from the great blue heron (*Ardea herodias*). J. Prasitol. 76: 717-724) and *Giardia microti* from muskrats and voles (van Keulen et al. 1998 The sequence of *Giardia* small subunit rRNA shows that voles and muskrats are parasitized by a unique species *Giardia microti*. J. Parasitol. 84: 294-300).

Sequence information of 18S rDNA of *Giardia lamblia* and phylogenetically closely related species was obtained from GenBank through ANGIS (Australian National Genomic Information Service) at Sydney University. All relevant sequences of *Giardia* spp. as available in April 2000 were examined. Sequences retrieved included:

Z17210-*Giardia ardea*
M54878-*Giardia lamblia;*
U09492-*Giardia lamblia*
U09491-*Giardia lamblia*
AF006677-*Giardia microti*
AF006676-*Giardia microti*
X65063-*Giardia muris*
U20351-*Giardia.* sp.
L16997-*Cryptosporidium parvum;*
L19069-*Cryptosporidium muris;*
L19068-*Cryptosporidium baileyi;*
U40261-*Cyclospora* sp.;
U40262-*Eimeria mitis;*
U40264-*Eimeria tenella;*
U40263-*Eimeria nieschulzi;*
U26532-*Nosema furnucalis;*
U26533-*Nosema ceranae;*
X73894-*Nosema apis;* and
L39110-*Ichtyosporidium*

Sequences were aligned using the program ClustalW and screened for diagnostic regions, e.g. regions that specifically discriminated *Giardia lamblia* from the other species included in the alignment. Six target regions were identified as listed below. The positions of the nucleotides given are not based on any internationally recognised numbering system but refer to the numbering for the *Giardia lamblia* 18S rRNA (designated 16S rRNA in the reference) given in a secondary structure model published by Sogin et al. in 1989 (Phylogenetic meaning of the kingdom concept: An unusual ribosomal RNA from *Giardia lamblia.* Science 243: 75-77). In accord with international agreements, all sequences listed, including oligonucleotide sequences, are shown in 5'-3' orientation.

Target Regions

Target regions (rDNA) were identified as follows:

```
1.  CCC GCT CAC CCG GGA CGC      (SEQ ID NO: 7)
    (Position 57-74)

2.  GGG CGG GCG CCC GCG GGC      (SEQ ID NO: 8)
    (Position 166-183)

3.  GCG AGC GAG GCG GGC CCA      (SEQ ID NO: 9)
    (Position 391-408)

4.  GTA GTT GGC CCC CCG CCG      (SEQ ID NO: 10)
    (Position 508-525)

5.  CAG GCC CGT TGG ACC CGC      (SEQ ID NO: 11)
    (Position 552-569)

6.  CGC GCC GCG GCA GCC CCG      (SEQ ID NO: 12)
    (Position 596-613)
```

Due to the fact that *G. lamblia* shows a very unusual 18 rRNA regarding sequence and secondary structure, it appeared reasonable to assume that the probes are *G. lamblia* specific and will not show cross reactions with other protozoans under moderately stringent hybridisation conditions. Table 1 shows a comparison of the target regions for the two functional FISH probes Giar-4 and Giar-6 from all *Giardia* spp. 18S rDNA/RNA target sequences available. A cross reaction observed from probe Giar-4 with *G. muris,* probably the phylogenetically closest related species to *G. lamblia,* occurred under low stringency hybridisation and was eliminated by increased stringency through 20% formamide in the hybridisation buffer. The alignment of published sequences used to design the probes showed that the corresponding target region of Giar-4 on the *G. muris* 18S rRNA shows eight mismatches and one deletion compared to the target region on the *G. lamblia* 18S rRNA. A corresponding target region for Giar-6 does not exist on the *G. muris* 18S rRNA. It appears that a large part of the rRNA in this region was deleted during the evolution of *G. muris.*

From database searches, it would appear that the Giar-4 and Giar-6 probes might cross react with a species designated *G. microti,* isolated from muskrats and voles. These sequences show a very high overall sequence homology up to 96.8% to the *G. lamblia* sequence. It appears questionable to describe the isolate as a species different to *G. lamblia* as other *Giardia* spp. share as little as 72-75% sequence homology *G. lamblia.* Given that it has not been demonstrated to date that *G. microti* does not infect humans, it appears possible that the organism is in fact *G. lamblia* or a subspecies of *G. lamblia* which is supported by the high sequence homology of the 18S rRNAs. According to literature available, *G. microti* is not a generally recognised species and the fact that Giar-4 and Giar-6 will detect the organism is unlikely to contradict the finding that the probes according to the present invention are *G. lamblia* specific.

TABLE 1

Comparison of the target regions of 'Giar-4' and 'Giar-6' on the 16S rDNA of *Giardia* spp.*

| Species/Accession | Target 'Giar-4' | Target 'Giar-6' |
|---|---|---|
| *G. lamblia* M54878 | GTAG TTGGCCCCCCGCCG (SEQ ID NO: 9) | CGCGC CGCGGCA GCCCCG (SEQ ID NO: 12) |
| *G. lamblia* U09492 | GTAG TTGGCCCCCCGCCG (SEQ ID NO: 9) | CGCGC CGCGGCA GCCCCG (SEQ ID NO: 12) |
| *G. lamblia* U09491 | GTAG TTGGCCCCCCGCCG (SEQ ID NO: 9) | CGCGC CGCGGCA GCCCCG (SEQ ID NO: 12) |

TABLE 1-continued

Comparison of the target regions of 'Giar-4' and 'Giar-6' on the 16S rDNA of *Giardia* spp.*

| Species/Accession | Target 'Giar-4' | Target 'Giar-6' |
|---|---|---|
| G. microti AF006677 | GTAG TTGGCCCCCCGCCG (SEQ ID NO: 9) | CTCGC CGCGGCA GCCCCG (SEQ ID NO: 16) |
| G. microti AF006676 | GTAG TTGGCCCCCCGCCG (SEQ ID NO: 9) | CGCGC CGCGGCA GCCCCG (SEQ ID NO: 12) |
| G. ardea Z17210 | GCAGGCGTCGCGCGGCGCTG (SEQ ID NO: 13) | TGGACCTACCGCCCGGGACGGCG (SEQ ID NO: 17) |
| G. sp. U20351 | GGCGCTGCTG CTGCAGTTA (SEQ ID NO: 14) | CGC C CGGGAC GCGCG (SEQ ID NO: 18) |
| G. muris X65063 | GGAGTCGAGACGTC CAG (SEQ ID NO: 15) | Not Applicable** |

Nucleotide residues printed in bold indicate mismatch to the G. lamblia target sequences of 'Giar-4' and 'Giar-6', blank space represents nucleotide deletions
*Analysis include all 16S rDNA sequences of *Giardia* spp. available through GenBank in April 2000
**Comparative sequence analysis and secondary structure modeling led to the conclusion that no corresponding target region exists on the 16S rRNA of *G. muris*

FISH Probes

Fluorescently labelled oligonucleotide probes were produced for the target regions as shown above. Naturally, sequences of the oligonucleotides are the reverse complement of the target regions:

| | | |
|---|---|---|
| Giar-1 | GCG TCC CGG GTG AGC GGG | (SEQ ID NO: 1) |
| Giar-2 | GCC CGC GGG CGC CCG CCC | (SEQ ID NO: 2) |
| Giar-3 | TGG GCC CGC CTC GCT CGC | (SEQ ID NO: 3) |
| Giar-4 | CGG CGG GGG GCC AAC TAC | (SEQ ID NO: 4) |
| Giar-5 | GCG GGT CCA ACG GGC CTG | (SEQ ID NO: 5) |
| Giar-6 | CGG GGC TGC CGC GGC GCG | (SEQ ID NO: 6) |

Preliminary investigations including a universal eukaryotic probe as a positive control showed that only probes Giar-4 and Giar-6 were suitable for FISH as the other probes yielded no or very weak signals. Subsequently, Giar-4 and Giar-6 were employed for further testing and refinement of hybridisation conditions. The other four probes, Giar-1, Giar-2, Giar-3, and Giar-5, however, can be employed for specific detection of *Giardia lamblia* rRNA or rDNA in techniques that target free nucleic acids such as Polymerase Chain Reaction (PCR) assays or dot blot hybridisations.

Results

Commercially available viable *Giardia lamblia* cysts were used. Aliquots of cysts were stored at −20° C. in 50% ethanol and 50% phosphate buffered saline (PBS), pH 7.2. This method of fixation enables long term storage (>1 year) prior to hybridisation experiments without diminished FISH signal due to degradation of ribosomal nucleic acids.

Method

Protocol for Fluorescent in situ Hybridisation in 1.5 ml Tubes

A suspension containing cysts was centrifuged for 5 min and the supernatant discarded. A centrifugal force greater than 1200×g should be avoided as this will cause many cysts to rupture.

Resuspend cysts in 50% ethanol and 50% PBS, incubate at 80° C. for 20 min.

Centrifuge cysts, discard supernatant and resuspend in FISH buffer (0.9 M NaCl, 10 mM Tris/HCl, pH 7.2, 0.1% SDS, 20% formamide). Adding 20% formamide to the hybridisation buffer increased the stringency sufficiently to eliminate the above mentioned cross reactions of the probes with *Giardia muris* containing 1 picomol per microliter of each fluorescently labelled probe Giar-4 and Giar-6.

Incubate at 80° C. for 2 min, transfer to 48° C. water bath and incubate 60 min.

Terminate hybridisation by adding ice cold PBS, spin, discard supernatant and resuspend cysts in ice cold PBS. Cysts are then ready to be examined.

The hybridisation protocol as detailed above can be applied for cysts concentrated via IMS, stained with FITC-labelled antibodies and sorted on filters by flow cytometry. Alternatively, *Cryptosporidium parvum* oocysts and *Giardia lamblia* cysts can be detected simultaneously by applying the specific probes described here in conjunction with *Cryptosporidium parvum* specific probes and hybridisation protocols (Deere et al. 1998 Rapid method for fluorescent in situ ribosomal RNA labelling of *Cryptosporidium parvum*. J. Appl. Microbiol. 85: 807-818; Vesey et al. 1998 The use of a ribosomal RNA targeted oligonucleotide probe for fluorescent labelling of viable *Cryptosporidium parvum* oocysts. J. Appl. Microbiol. 85: 429-440).

Modifications

Possible modifications of the invention is the application of methods that allow amplification of the fluorescent FISH signal. In brief, molecular beacons are modified, fluorescently labelled oligonucleotides that can only emit a fluorescent signal when attached to their specific nucleic acid target. No signal will be obtained from probes that are bound non-specifically to any other matter in a sample. In essence, increased signal strength is achieved by eliminating or at least drastically reducing background signals (Schofield et al. 1997 Molecular beacons: Trial of a fluorescence-based solution hybridization technique for ecological studies with ruminal bacteria. *Appl. Envir. Microbiol.* 63: 1143-1147). Tyramide signal amplification (Schönhuber et al. 1997 Improved sensitivity of whole cell hybridization by the combination of horseradish peroxidase-labelled oligonucleotides and tyramide signal amplification. *Appl. Envir. Microbiol.* 63: 3268-3273) utilises unlabelled oligonucleotide probes that are conjugated to horseradish peroxidase (HRP). After the hybridisation reaction is completed, the hybridisation buffer is removed and replaced by a buffer solution containing HRP substrate conjugated to a fluorescent dye. Subsequently, HRP linked to oligonucleotides converts the substrate into a fluorescent precipitate that accumulates in the target cells.

The present invention is a continuation of the development of specific oligonucleotide probes for detection and enumeration of protozoan pathogens in water via fluorescent in situ hybridisation (FISH). The investigations led to the first specific FISH probes for detection of viable *Cryptosporidium parvum* oocysts (WO 96/34978 entitled Method for the Detection of Viable *Cryptosporidium parvum* oocysts). Comparative sequence analysis of the 18S ribosomal DNA (rDNA) from *Giardia lamblia* and closely related species (in terms of sequence homology) and secondary structure analysis was used to determine the accessibility of the potential target region resulted in the oligonucleotide probes disclosed. Based on the above investigations, six potentially specific FISH probe sequences were determined. The probes were produced and tested on trophozoites of *Giardia lamblia*. Two of these probes (designated Giar-4 and Giar-6) yielded a strong fluorescent signal and showed the same result when hybridised against potentially viable cysts. The remaining four probes showed either very weak or no fluorescence at all and were subsequently omitted from further FISH experiments. However, these four probes can be employed for specific detection of *Giardia lamblia* rRNA or rDNA in techniques that target free nucleic acids such as Polymerase Chain Reaction (PCR) assays or dot blot hybridisations.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An oligonucleotide molecule for the detection of Giardia lamblia (G. lamblia), wherein the oligonucleotide molecule consists of either CGGCGGGGGGCCAACTAC (SEQ ID NO: 4) or CGGGGCTGCCGCGGCGCG (SEQ ID NO: 6), wherein either may be detectably labeled.

2. The oligonucleotide molecule according to claim 1 wherein the oligonucleotide molecule is detectably labeled.

3. The oligonucleotide molecule according to claim 2 wherein the label is selected from the group consisting of fluorochrome, radioisotope, and chemical.

4. The oligonucleotide molecule according to claim 3 wherein the label is a fluorochrome.

5. The oligonucleotide molecule according to claim 3 wherein the fluorochrome is selected from the group consisting of fluorescein isothiocyanate (FITC, green), cyanine dyes Cy2, Cy3, Cy3.5, Cy5, Cy5.5 that range from green to far red, and Texas Red.

* * * * *